(12) United States Patent
Cordaro

(10) Patent No.: US 7,220,263 B2
(45) Date of Patent: May 22, 2007

(54) CERVICAL PLATE/SCREW SYSTEM FOR IMMOBILIZING VERTEBRAL BODIES

(75) Inventor: Nicholas M. Cordaro, Cardiff by the Sea, CA (US)

(73) Assignee: SeaSpine, Inc., Vista, CA (US)

( * ) Notice: Subject to any disclaimer, the term of this patent is extended or adjusted under 35 U.S.C. 154(b) by 471 days.

(21) Appl. No.: 10/679,012

(22) Filed: Oct. 3, 2003

(65) Prior Publication Data
US 2004/0068319 A1    Apr. 8, 2004

Related U.S. Application Data

(60) Provisional application No. 60/416,225, filed on Oct. 4, 2002.

(51) Int. Cl.
*A61B 17/58* (2006.01)

(52) U.S. Cl. .......................................... 606/69; 606/61

(58) Field of Classification Search .................. 606/69, 606/70, 71
See application file for complete search history.

(56) References Cited

U.S. PATENT DOCUMENTS

| | | | |
|---|---|---|---|
| 5,364,399 A * | 11/1994 | Lowery et al. ............... | 606/69 |
| 5,578,034 A | 11/1996 | Estes | |
| 5,601,553 A | 2/1997 | Trebing et al. | |
| 5,683,393 A * | 11/1997 | Ralph ......................... | 606/61 |
| 5,876,402 A | 3/1999 | Errico et al. | |
| 5,904,683 A | 5/1999 | Pohndorf et al. | |
| 5,954,722 A | 9/1999 | Bono | |
| 6,129,730 A | 10/2000 | Bono et al. | |
| 6,139,550 A | 10/2000 | Michelson | |
| 6,235,033 B1 | 5/2001 | Brace et al. | |
| 6,235,034 B1 | 5/2001 | Bray | |
| 6,428,542 B1 * | 8/2002 | Michelson ................... | 606/70 |
| 6,695,846 B2 * | 2/2004 | Richelsoph et al. .......... | 606/71 |

OTHER PUBLICATIONS

Commercial specimen of an Orion surgical plate with one screw per U.S. Patent No. 5,364,399. The plate is also illustrated in Nicholas M. Cordaro's declaration dated Feb. 5, 2007.
Commercial specimen of a buttress plate made in accordance with the subject application by the Assignee SeaSpine, Inc. The plate is not prior art.

* cited by examiner

*Primary Examiner*—Eduardo C. Robert
*Assistant Examiner*—James L. Swiger
(74) *Attorney, Agent, or Firm*—Harold L. Jackson

(57) ABSTRACT

A plate/screw system for immobilizing adjacent vertebral bodies or an interbody device includes a plate having at least one spaced opening with an upper section of a width or diameter of $d_1$ and a lower section having or diameter less than $w_1$. The lower section defines a partial or completed helical track for receiving a screw. A bone screw for insertion into the threaded opening has a head section of $d_1$, an adjacent neck section of $d_2$ and a thread section of $d_3$ where $d_2<d_3<d_1$ whereby the relationship between $d_1$ and $w_1$ determines whether the screw can or cannot pivot relative to the plate.

28 Claims, 7 Drawing Sheets

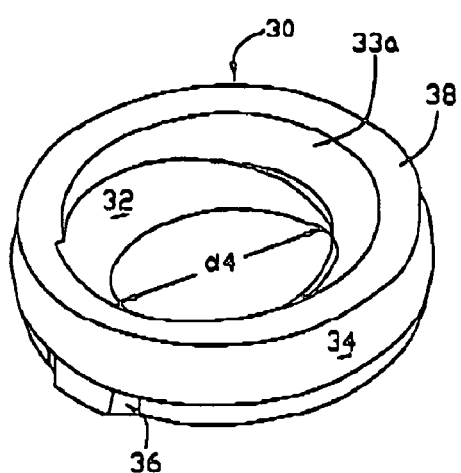
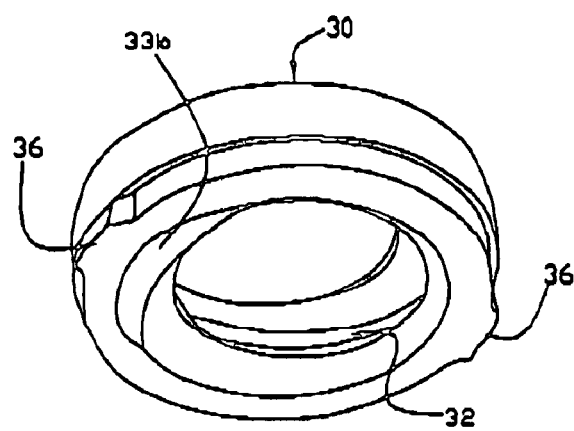
Figure 5
Figure 6
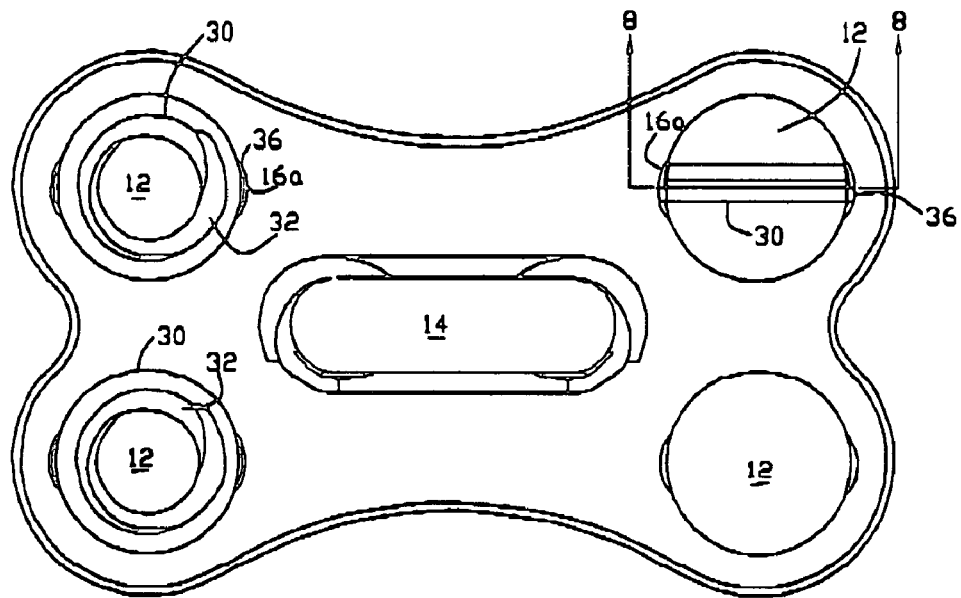
Figure 7

CERVICAL PLATE/SCREW SYSTEM FOR IMMOBILIZING VERTEBRAL BODIES

RELATED APPLICATION

This application claims the benefit of the filing date of provisional application No. 60/416,225 filed Oct. 4, 2002 entitled PASSING THREAD LOCKING FIXATION DEVICE as to all common subject matter.

FIELD OF THE INVENTION

The present invention relates generally to a plate system useful, for example, to fuse segments of the human cervical spine or to stabilize an adjacent interbody device from the anterior aspect. More specifically the invention relates to a device used to align and maintain the alignment between adjacent vertebrae and interbody device where applicable in a predetermined spatial relationship by a qualified surgeon during spinal fusion.

BACKGROUND OF THE INVENTION

Current practice in the art of cervical spinal fusion is to use a cervical plate which secures adjacent vertebrae. These systems typically use multiple screws which attach the vertebrae body and occasionally bone graft to the plate. The surgeon decides upon the spatial orientation through manipulations, and then affixes the securing plate. Plates are generally designed to place 2 screws into each vertebra body. Some plates allow the screw(s) to be placed in only one or in up to a maximum of four unique locations per body. The screws are prevented from "backing out" or becoming removed from the plate by various locking or blocking means. Plate and screw combinations allow for screws to be placed at a fixed or variable angle relative to the plate. A few plates allow for a dynamic settling of the vertebrae bodies by allowing screws positioned in adjacent vertebra bodies to approach. This is accomplished by either allowing the screws to slide within the plate or by allowing the plate to compress in a telescopic manner.

SUMMARY OF THE INVENTION

It is an object of the invention to provide a plate system, i.e., plate, and screw combination capable of providing a reliable and simplistic means of securing adjacent vertebrae bodies or interbody device during spinal fusion. Fixed, variable, and dynamic screw and plate combinations are included.

It is a further object to provide a secure means of attaching a fixation plate to separated or partially separated vertebral bodies by means of a threaded screw device which may continue to rotate after firmly inserted through the plate, allowing the plate to be drawn tightly onto the bodies. Installation and removal of the screws are only permissible through axial rotation of the screw, and not axial (i.e., along the longitudinal axis) or transverse (i.e., in a plane perpendicular to the longitudinal axis) loading.

Another object is to provide a system accommodating different screw designs, e.g., (a) screws which remain at a fixed angle to the plate, (b) screws which are allowed to angulate or pivot relative to the plate and (c) screws and an associated plate design that allows the screws to angulate and traverse relative to the plate.

A plate system for immobilizing adjacent vertebral bodies in accordance with the present invention includes a plate having at least one opening therein spaced to overlie the vertebrae bodies to be immobilized. Each opening has an upper section with a preselected width $w_1$ for receiving the head section of a cervical screw and a threaded lower section which may include a screw receiving ring therein, has a width less than $w_1$ and defines at least a partial helical track through which the threaded end of the screw may be threaded.

A bone screw for use with the plate has a cylindrical head section of one diameter, an intermediate neck section of a second diameter and a depending thread section of a third diameter. The threaded section of the screw has a pitch matching the pitch of the partial helical track in the plate. The neck diameter of the screw has a smaller diameter than that of the head section or the screw head with the threaded section of the screw being arranged so that once the screw is threaded completely into the plate opening the screw may be rotated relative to the plate without causing any axial movement between the screw and plate.

BRIEF DESCRIPTION OF THE DRAWINGS

FIGS. 5 and 6 are top and bottom perspective views, respectively, of a screw receiving ring adapted to be inserted into the ring receiving openings in the plate for allowing the screw to rotate relative to the plate without axial movement;

FIG. 7 is a bottom plan view of the plate of FIG. 1 illustrating the manner in which a screw receiving ring may be installed in an associated opening in the plate (top right);

DESCRIPTION OF THE PREFERRED EMBODIMENT

Figure 2:
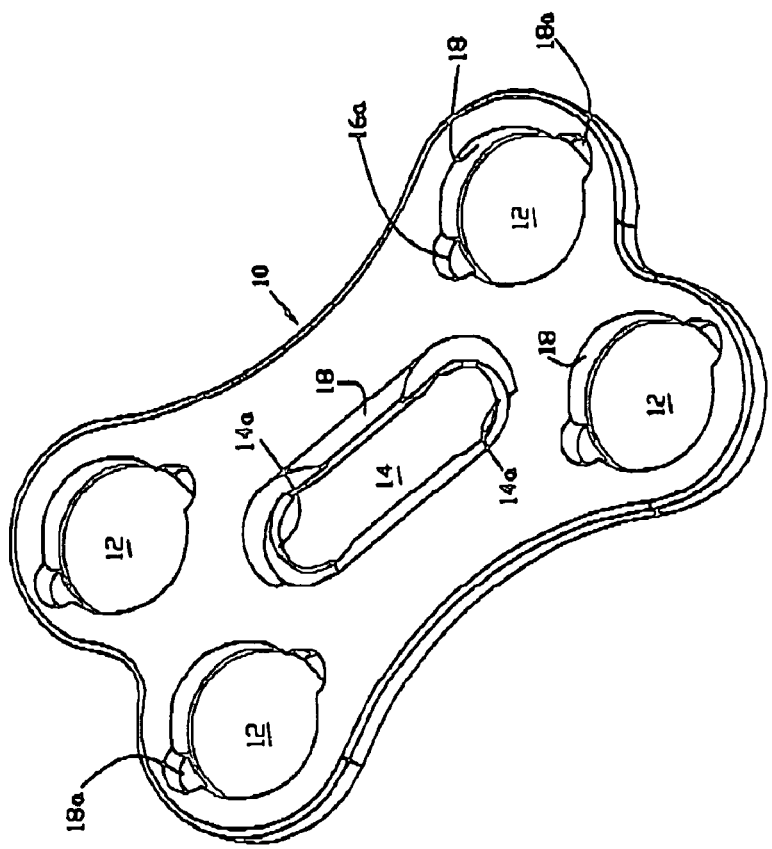
FIG. 2 is a bottom perspective view of the plate of FIG. 1.
Figure 1:
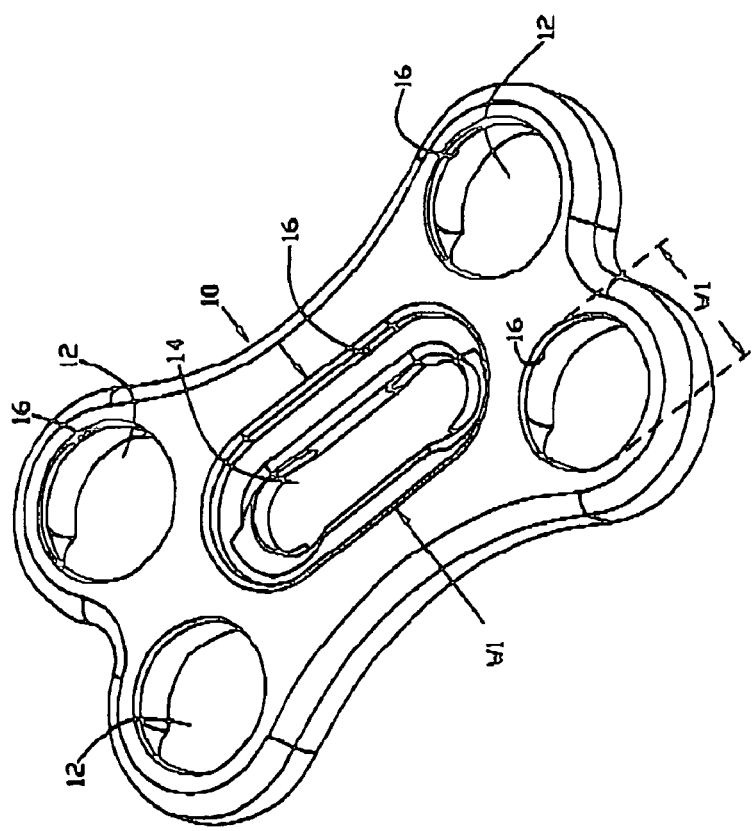
FIG. 1 is a top perspective view of a cervical plate adapted to receive screw receiving rings in the four outermost holes and a screw in the center slot in accordance with the invention.

Referring now to the drawings and particularly to FIGS. 1 and 2, a cervical plate 10 has openings 12 adapted to be located over two adjacent vertebral bodies (not shown), and an additional opening in the form of a slot 14 adapted to span the distance between adjacent vertebral bodies. Each of the circular openings have an upper section 16 with a pre-selected width $w_1$ (or diameter if circular as is the case with the openings 12) for receiving the head of a screw to be described. The openings further have lower sections 18a and 18b for the openings 12 and 14, respectively. The lower sections 18a define an internal arc or spherical inner surface in cross-section which accommodates a ring (to be described) and allows the ring to pivot or angulate relative to the plate as will be explained.

The lower section 18b of the slotted opening 14 defines a partial helical track 14a thread on each end through which a screw may be threaded as will be described. The $w_2$ of the slot 14 between the helical end tracks is wider than the neck of the screw to be inserted into the track, but narrower than the threaded shaft of the screw to be described in conjunction with FIG. 10. The width of the slot allows the screw to travel along the slot and allow vertebral bodies to settle during fusion. The partial helical tracks are adapted to accommodate one screw each. Diametrically opposing notches 16a (FIG. 2) are formed in the lower sections 16 of the openings 12 to receive fit anti-rotation tabs on rings to be inserted into the lower sections of openings 16 as will be described.

Figure 3:
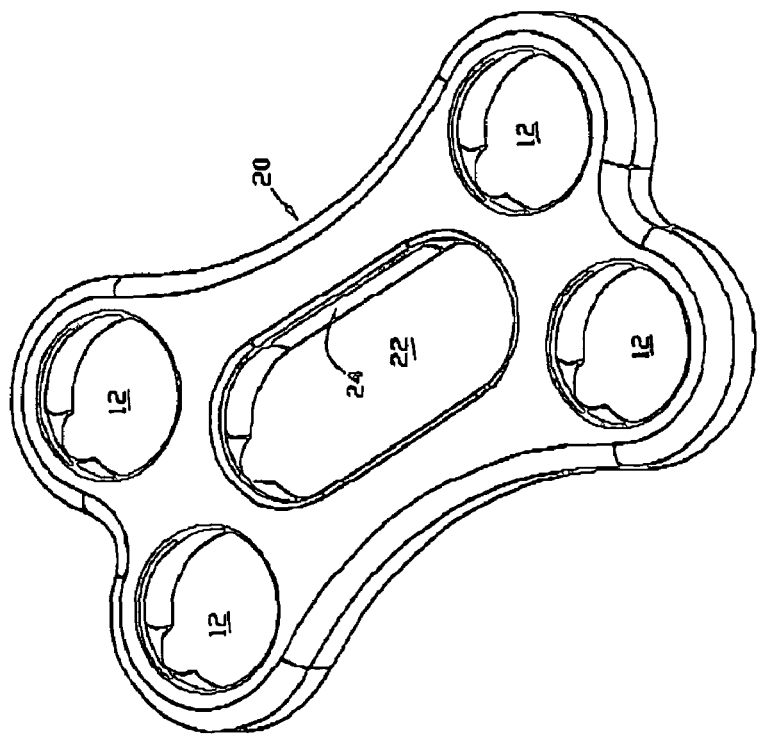
FIG. 3 is a top perspective view of an alternate embodiment of the plate for accommodating a slidable ring/screw in the center slot.

A modified plate 20 is illustrated in FIG. 3 in which the central opening or slot 22 has a lower section 24 which is arranged to receive one or possibly two screw receiving rings allowing the ring/screw assembly to translate along the slot much like screws could translate along the slot 14 of the plate 10 of FIGS. 1 and 2.

Figure 4:
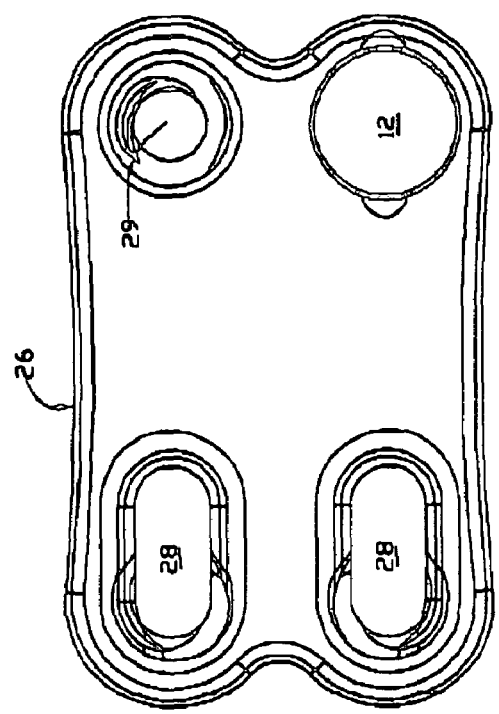
FIG. 4 is a top plan view of an alternate embodiment of a plate with two screw receiving slots on the left side, an opening on the lower right side for accommodating a ring receiving screw and a opening on the upper right for receiving a screw per se.

Referring to FIG. 4 an alternative plate 26 is provided with an opening 12, the lower section thereof being arranged to accommodate a screw receiving ring, two slotted openings 28 and a circular opening 29, each of the latter having threaded lower sections arranged to receive a screw directly, as will be described.

The preceding figures illustrate only basic plate variations capable of fusing only two adjacent vertebrae, or a one level fusion. The plate could be extended to multiple levels to aid multiple level fusion or reduced to only attach to one vertebrae body and overhang into the disk space to buttress or stabilize an interbody device. Multiple variations are possible regarding screw hole locations, ring locations, and slotted ring locations. For example, a three or four level plate may contain two parallel slots rather than spherical holes at the screw locations in order to allow the vertebrae bodies to settle during fusion.

Referring now to FIGS. 5 and 6 (top and bottom views) a screw receiving ring 30 for insertion into the lower sections of certain of the plate openings, i.e., 12, described previously, forms the lower helical thread section 32 of the plate opening. It is to be noted that the term plate as used herein encompasses a plate with one or more rings installed in the lower section of the associated openings or a plate in which the lower sections of one or more openings are threaded directly to receive the screws.

The ring is provided with top and bottom chamfers 33a and 33b, respectively. The chamfers match corresponding chamfers merging with the neck of a screw as will be described in the discussion of FIG. 10. It is to be noted that the threads 32' and chamfers 33a and 33b comparable to the threads and chamfers (32, 33a and 33b) may be formed directly in the lower sections of the plate openings, such as opening 29, for receiving a screw directly.

Figure 13:
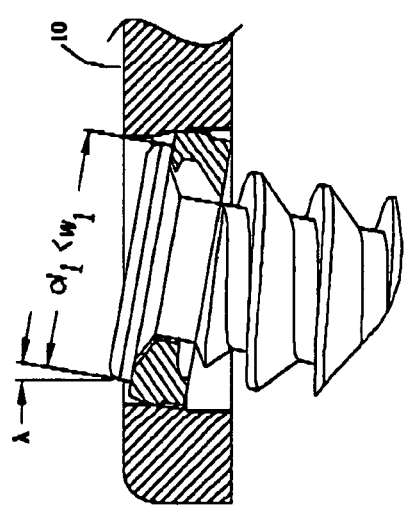
FIG. 13 is a cross-sectional view of a variable angle screw/plate/ring assembly.
Figure 15:
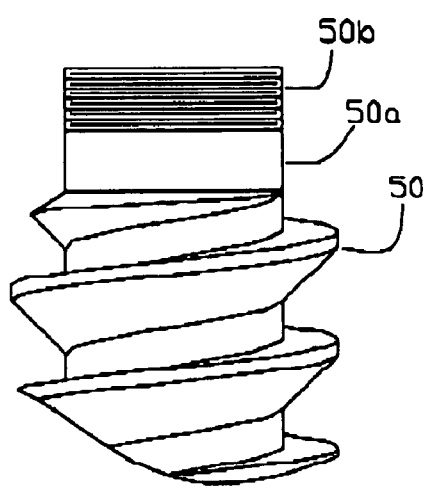
FIGS. 15–18 illustrate several views of an alternate embodiment of a screw having a separate head section with FIGS. 15 and 16 showing the lower section of the screw, partially broken away and in cross section in FIG. 16, and with FIGS. 17 and 18 showing a plan and side view respectively of the top disk section of the screw
Figure 16:
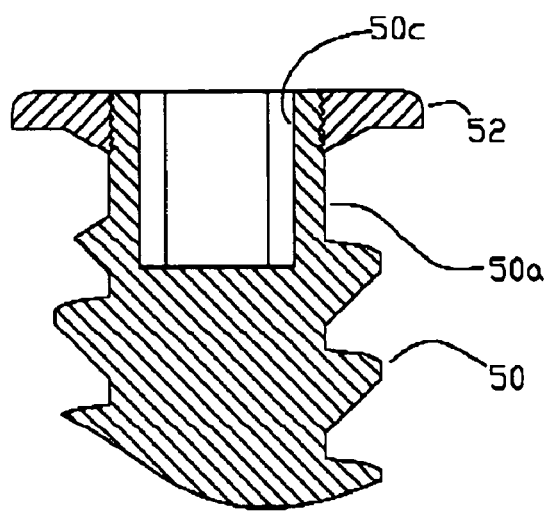
Figure 17:
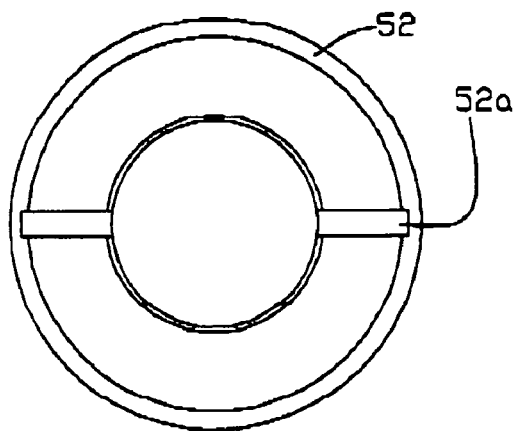
Figure 18:
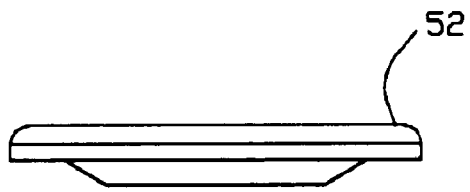

The upper peripheral surface 34 of the ring 30 matches the annular interior spherical surface 18a of the lower section of the plate openings designed to accommodate rings, e.g., openings 12, 22. See FIGS. 1 and 9. The cooperating spherical surfaces allow the ring to pivot in a circular manner relative to the plate as is illustrated in FIG. 13. The ring 30 has radially protruding anti-rotation tabs 36 on the bottom end thereof as is illustrated in FIGS. 5 and 6. These tabs are adapted to be inserted into the cooperating receptacles or cavities 18c in the lower section of the ring accommodating openings of the plate to prevent the rings from rotating in response to the rotation of a screw therein. In addition, there is press or friction fit between the tabs 36 and the cavities 18c to maintain the rings in place within the plate openings after installation. It is to be noted that the tabs do not prevent the rings from pivoting within the plate openings as is illustrated in FIG. 13. It is to be noted that the anti-rotation feature of the rings/plate openings can be accomplished in other ways, e.g., the tabs could extend frm the plate to the ring, a wedge could be inserted between the cooperating surfaces of the ring and plate opening or friction forces between such surface may be sufficient to prevent ring rotation.

Figure 8:
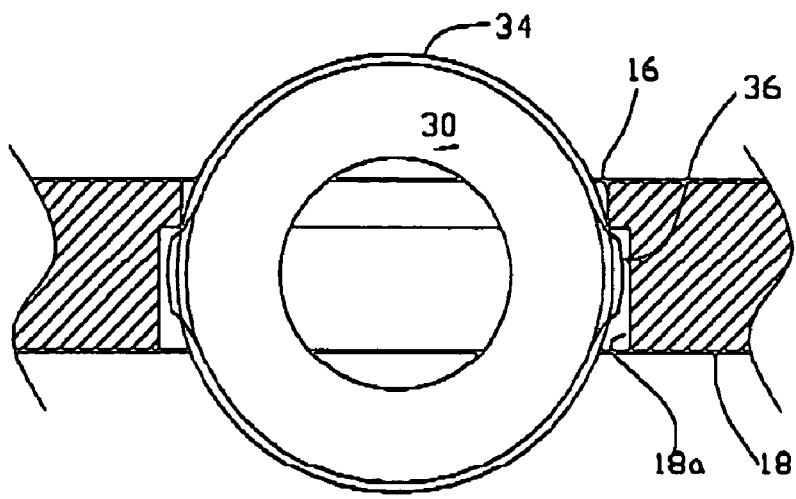
FIG. 8 is a cross-sectional view taken along lines 8—8 of FIG. 7 illustrating the manner in which a press fit between the anti-rotation tabs on the ring and the respective receptacle pockets in the plate openings hold the ring in place and prevent it from rotating.
Figure 9:
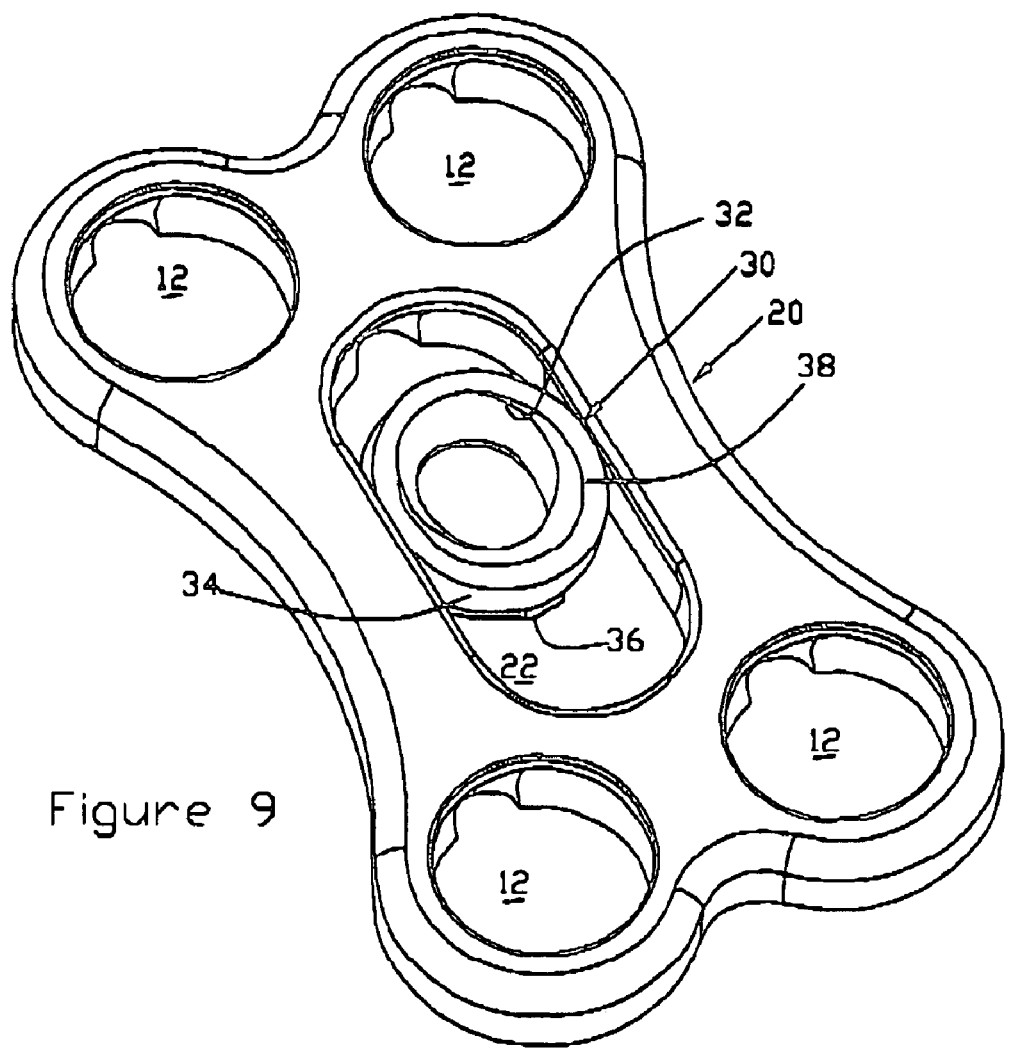
FIG. 9 is a top perspective view of the plate of FIG. 3 with a screw receiving ring installed in the center slot.

The ring shown in FIGS. 5 and 6 may be inserted into an associated plate opening by first positioning the top surface 35 (or bottom surface 37) perpendicular to the plate, as shown in the upper left opening of the plate of FIG. 7, so that the anti-rotation tabs 36 rest within the transverse notches 18c and so that one side of the ring extends through the center of the opening. The ring is then rotated 90 degrees to rest relatively parallel to the plane of the plate. The openings on the left side of the plate shown in FIG. 7 have rings installed in the lower sections thereof FIG. 8 is an enlarged view partially in cross-section taken along lines 8—8 of FIG. 7 illustrating the initial installation step of installing a ring into the lower section of an opening 12. FIG. 9 illustrates the plate of FIG. 3 with a ring 30 installed in the lower section of the opening 22.

Figure 10:
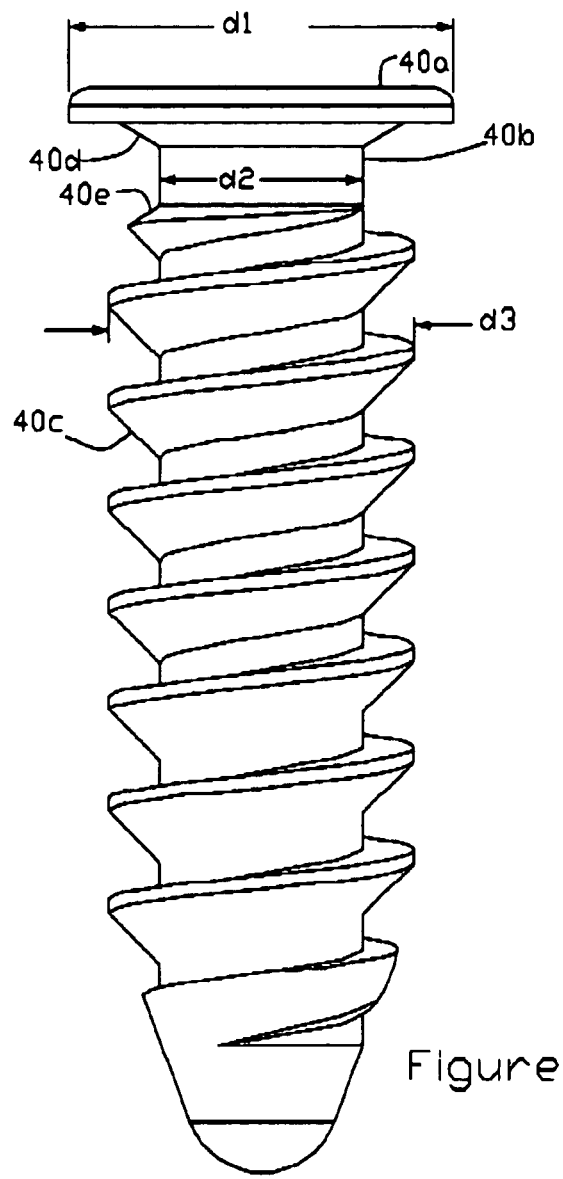
FIG. 10 is a front elevational view of a generic screw, e.g., fixed or variable angle, for use with the associated openings in the plate/rings.

Referring now to FIG. 10 there is illustrated a screw 40 for use with a plate in which the lower sections of the openings define threads in the wall of the plate, as is the case with the opening 29 of FIG. 4 or the center slot of the plate of FIG. 1 or with a ring 30. The screw 40 includes a disk-shaped head 40a having a diameter $d_1$, an unthreaded neck 40b having a diameter $d_2$, a threaded lower shaft 40c with an outside diameter $d_3$. The threads may, for example, be self tapping fluted bone threads with either single or double pitch.

The unthreaded neck 40b allows a fully seated screw, i.e., inserted into the plate (with internal threads or with a ring) to continue to rotate without the threads thereof engaging the threads in the plate or ring. Thus, the screw, once fully inserted, will not translate or move axially (along the screw's longitudinal axis x—x) relative to the plate or ring during rotation. See FIG. 11.

Figure 11:
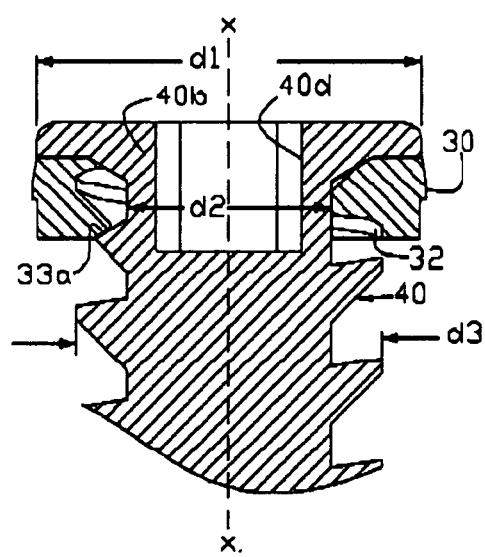
FIG. 11 is a side elevational view partially broken away and in cross section of an assemble ring and screw.

The screw includes chamfers 40d and 40e which match the ring chamfers 33a and 33d, respectively. The chamfers allow the screw, once installed, to rotate in the ring without moving axially of the ring. FIG. 11 illustrates a screw 40 fully inserted into a ring 30. The upper chamfer 33a of the ring in addition to allowing the screw to rotate freely of the ring, once installed, acts as a guide for starting the screw through the ring. It should be noted that the chamfers are not required and could be replaced by a stepped relief between the screw head and the threads.

The diameter $d_1$ of the screw head relative to the width or diameter $w_1$ of the plate upper section opening determines whether or not the screw is fixed, i.e., cannot pivot to any substantial degree within the plate opening or is variable, i.e., allowed to pivot within the opening. Where $d_1$ is substantially equal (but slightly smaller) than $w_1$ (hereinafter $d_1 \cong w_1$), the screw can not pivot to any substantial degree, i.e., the screw is classified herein as a fixed screw. Where $d_1 < w_1$ the screw can pivot within the opening, i.e., the screw is classified herein as variable. The fixed angle screw design with its upper cylindrical section (screw head) 40a (FIG. 10) having a diameter $d_1$ (~0.222") about equal to the diameter or width $w_1$ of the supper section 16 of the opening in the plate (~0.224) prevents any pivotal movement of the screw when completely inserted into the ring. The head diameter $d_1$ of the variable screw would be further undersized (~0.200") as to allow for a desired variable angle relative to the plate's tangent direction (FIG. 13).

Figure 12:
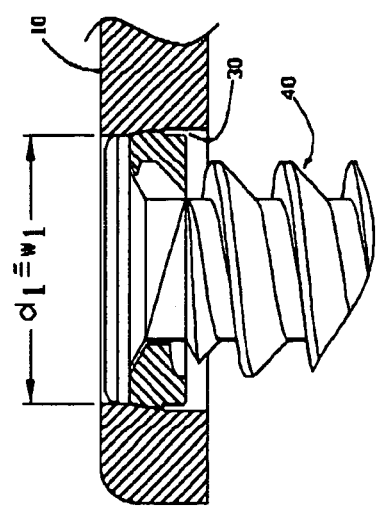
FIG. 12 is a cross-sectional view of a fixed angle screw/plate/ring assembly.

Fixed and variable screws, as classified herein, are illustrated in FIGS. 12 and 13, respectively, with the variable screw having a $d_1 < w_1$ being able to pivot relative to the plate 10 (FIG. 13) while the fixed screw having a $d_1 \cong w_1$ is not able to pivot (FIG. 12). A dynamic screw like a variable screw has a head diameter $d_1 \cong w_1$ or $d_1 < w_1$. The distinction is that a dynamic screw when positioned within a slotted opening such as the opening 14 in FIG. 1 laterally along the slot, one installed through the partial helical track 14a.

Figure 14:
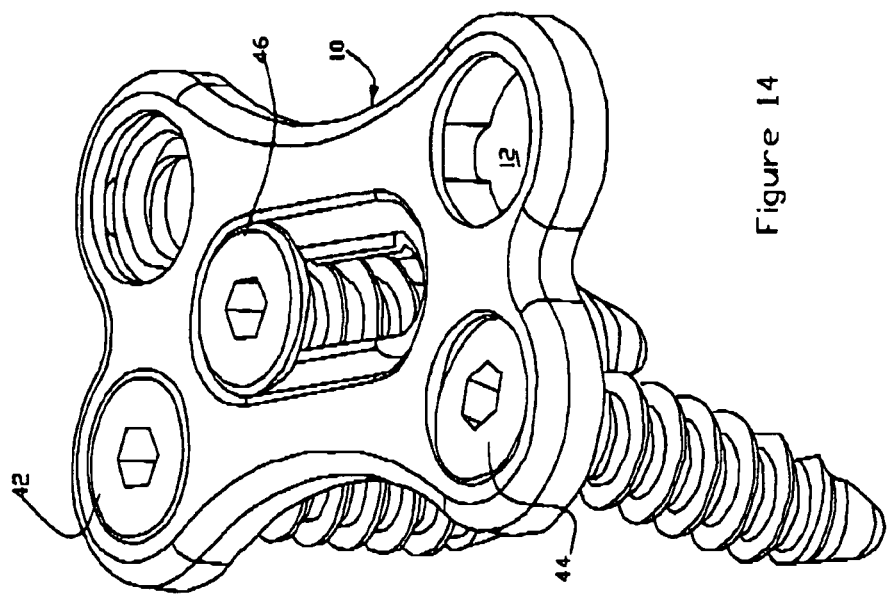
FIG. 14 is a top perspective view of the plate of FIG. 1 with fixed, variable and dynamic screws and associated rings in place.

Examples of fixed, variable and dynamic screws, 42, 44 and 46, respectively, as installed in a plate 10 (FIGS. 1 and 2) is illustrated in FIG. 14. The fixed screw 42 cannot pivot while the variable screw 44 can. The dynamic screw with a head section wherein $d_1 < w$ can not only pivot, but move laterally along the slot 14.

It is noted that a plate with a single opening such as 29 of FIG. 4 can be used with a single screw, the screw and the lower section of the plate opening having the chamfers, discussed previously, to buttress a single vertebrae or interbody device. The chamfers prevent the screw from backing out of the plate.

FIGS. 15–18 illustrate an alternate screw arrangement, i.e., a two part screw comprising a lower screw threaded section 50 and a locking top disk 52. Section 50 includes a neck 50a, which serves the function previously described and a top threaded portion 50b on which the disk section 52 is threaded to complete the assembly. The locking top disk 52 may be rotated via the opposing notches 52a independently after the screw is threaded into the threaded opening in the lower section of the plate (with or without a ring) to firmly clamp and create a rigid fixation to the plate. The plate, screw and ring (where used) is preferably made of titanium.

In summary, the invention comprises a cervical plate with openings having lower threaded sections (at least on one end where the opening is a slot) incorporated directly in the plate or via an installed ring and a fixed angle or variable angle screw. Both screws may serve as a transverse sliding or dynamic screws when positioned inside of a slotted opening. The threads of the screws are allowed to pass entirely through the plate (and ring where incorporated into the plate) by means of axial rotation. A fully seated screw will not have interlocking threads with the plate and the user may continue to rotate the screw to fully seat or pull the plate against the vertebrae bodies. The chamfers on the plate/ring and adjacent the neck (top and bottom) of the screws will not allow the screw to back out of the plate/ring by means of an axial or transverse load. This essentially locks the screw to the plate without the need for a secondary locking mechanism. A fixed screw, that will not rotate, may be held in a rigid position by a secondary locking mechanism incorporated into the screw head as is illustrated in FIGS. 15–18, if necessary.

What is claimed is:

1. A plate system for immobilizing adjacent vertebral bodies or stabilizing an interbody device, comprising:
   a plate having at least one opening therein, said at least one opening having an upper section with a preselected width $w_1$ for receiving the head section of a bone screw and a lower section having a width less than $w_1$ and defining at least a partial helical track through which the threaded end of the screw may be threaded; and
   a bone screw having a cylindrical head section of diameter $d_1$, an intermediate neck section of a diameter $d_2$ and a depending threaded section of a diameter $d_3$, the threaded section having a pitch matching the pitch of the at least the partial helical track in the plate, where $d_3 < d_1$, the threaded section of the screw being arranged so that once the screw is threaded completely into the plate opening the screw may be rotated relative to the plate to thread the screw into the vertebral body without causing any axial movement between the screw and the plate and may be removed from the plate only by reversing its rotation into said at least partial helical thread.

2. The invention of claim 1 wherein said at least one opening comprises a plurality of openings and wherein the openings overly the vertebral bodies to be immobilized.

3. The invention of claim 2 where $d_1 \cong w_1$ to substantially prevent the screw from pivoting relative to the plate when threaded completely into the plate opening.

4. The invention of claim 3 wherein at least one of the plate openings is generally cylindrical with $w_1$ equal to the diameter of the upper section of the opening and the lower section defining a complete helical thread.

5. The invention of claim 3 wherein at least one of the plate openings is in the form of a rectangular slot containing at least one partially threaded section therein.

6. The invention of claim 5 wherein the slot and screw are arranged so that the screw can traverse along the slot once threaded into the opening.

7. The invention of claim 3 wherein at least one of the plate openings is in the form of a rectangular slot terminating at least at one end in a semicircular portion containing the partially threaded section.

8. The invention of claim 2 where $d_1 < w_1$ to allow the screw to pivot relative to the plate when threaded completely into the plate opening.

9. The invention of claim 8 wherein at least one of the plate openings is generally cylindrical with $w_1$ equal to the diameter of the upper section of the opening and the lower section defining a complete helical thread.

10. The invention of claim 8 wherein at least one of the plate openings is in the form of a rectangular slot terminating at least at one end in a semicircular portion containing the partially threaded section.

11. The invention of claim 8 wherein at least one of the plate openings is in the form of a rectangular slot containing at least one partially threaded section therein.

12. The invention of claim 11 wherein the slot and screw are arranged so that the screw can traverse along the slot once threaded into the opening.

13. The invention of claim 1 wherein the partial helical thread is defined by a ring removably insertable into the lower section of the opening.

14. The invention of claim 1 wherein the entry and exit portions of the at least partial helical thread are in the form of an upper and lower chamfer, respectively, and wherein the screw has upper and a lower chamfer portions joining the neck to the cylindrical head and to the depending threaded portions, respectively, and the upper chamfer portion of the opening and the screw being complementary and the lower chamfer portions of the opening and the screw being complementary.

15. The invention of claim 1 where the head section of the screw is movable along the neck of the screw so that it may axially compress the plate against an underlaying vertebrae and rigidly fix its location.

16. The invention of claim 1 wherein said at least one opening in the plate includes a screw receiving ring forming the lower section thereof.

17. A cervical plate system for immobilizing adjacent vertebral bodies comprising:
a bone screw having a cylindrical head section of a first diameter $d_1$, an intermediate cylindrical neck section of a second diameter $d_2$, and a depending threaded section having a given pitch, the threads having an outside diameter of $d_3$, where $d_2$ is less than $d_1$ or $d_3$, the screw having an upper chamfer portion joining the cylindrical head section to the neck section and a lower chamfer portion joining the neck section to the depending threaded section;
a plate having at least two spaced openings therein for overlying vertebral bodies to be immobilized, each opening having an upper portion for receiving the head section of the screw and a lower portion defining at least a partial helical thread having the same pitch as the screw thread with entry and exit portions which have chamfers complementary to the upper and lower chamfer portions of the screw, the threads on the screw being arranged to extend below the exit portion of the at least partial helical thread in the plate opening whereby once the screw is threaded completely into the plate opening the screw may be rotated relative to the plate in a direction to thread the screw into a vertebral body without causing axial movement between the screw and plate and may be removed from the plate only by reversing its rotation into said at least partial helical thread.

18. The invention of claim 17 wherein at least one of the openings is in the form of a slot with semicircular ends and an intermediate generally straight section, the chamfers and the at least partial helical thread being formed on one of the semicircular ends.

19. The invention of claim 17 wherein at least one of the openings in the plate is generally cylindrical, the chamfers in the opening and at least the partial helical thread being formed by a ring inserted into the lower portion of the opening.

20. The invention of claim 19 wherein the upper portion of the plate opening has a diameter slightly greater than $d_1$ to substantially prevent any pivoting action of the screw within the opening once the screw has been completely inserted into the plate.

21. The invention of claim 19 wherein the upper portion of the plate opening has a diameter sufficiently less than $d_1$ to allow the screw to pivot within the opening once the screw has been completely inserted into the plate.

22. The invention of claim 19 where the head section of the screw is movable along the neck of the screw so that it may axially compress the plate, rigidly fixing its location.

23. A plate system for immobilizing adjacent vertebral bodies or stabilizing an interbody device comprising:
a bone screw having a cylindrical head section of a first diameter $d_1$, an intermediate cylindrical neck section of a second diameter $d_2$, and a depending threaded section having a given pitch, the threads having an outside diameter of $d_3$, where $d_2$ is less than $d_1$ or $d_3$;
a plate having at least one opening therein for attachment to a vertebral body and overlying an adjacent vertebral body and/or interbody device to be immobilized, the opening having an upper section for receiving the head section of the screw and a lower section defining at least a partial helical thread having the same pitch as the screw thread of the depending threaded section with entry and exit portions, the threads on the screw being arranged to extend below the exit portion of the at least partial helical thread in the plate opening whereby once the screw is threaded completely into the plate opening the screw may be rotated relative to the plate in a direction to thread the screw into a vertebral body without causing axial movement between the screw and plate and the screw may be removed from the plate only by reversing its rotation into said at least partial helical thread.

24. The invention of claim 23 wherein the at least partial helical thread comprises a complete helical thread.

25. The invention of claim 24 wherein said at least one opening is in the form of a slot and the helical thread being formed by a ring positioned therein, the slot being arranged to allow the ring and screw to move transversely along the slot.

26. The invention of claim 24 wherein said at least one opening is circular and the helical threading formed by a ring positioned therein, the lower section of said opening defining an anti-rotation cavity and the ring defining an anti-rotation tab which projects within the cavity to prevent the ring from rotating within the opening.

27. The invention of claim 23 wherein the upper section of the plate opening has a width of $w_1$ and $d_1 \cong w_1$ to substantially prevent the screw from pivoting relative to the plate when threaded completely into the plate opening.

28. The invention of claim 23 wherein $d_1 < w_1$ to allow the screw to pivot relative to the plate when completely threaded into the plate opening.

* * * * *